United States Patent [19]
Kamhi

[11] Patent Number: 4,547,317
[45] Date of Patent: Oct. 15, 1985

[54] POLY(ETHYLENEOXY)-SUBSTITUTED-9,10-BIS(PHENYLETHYNYL)ANTHRACENE MIXTURES

[75] Inventor: Victor M. Kamhi, Skillman, N.J.

[73] Assignee: American Cyanamid Company, Stamford, Conn.

[21] Appl. No.: 588,265

[22] Filed: Mar. 12, 1984

Related U.S. Application Data

[62] Division of Ser. No. 436,210, Oct. 25, 1982.

[51] Int. Cl.[4] ............................................. C09K 11/06
[52] U.S. Cl. .................................................. 252/700
[58] Field of Search ....................... 568/611, 808, 660; 252/700

[56] References Cited

U.S. PATENT DOCUMENTS 4,450,305  5/1984  Kamhi ................................. 568/611

*Primary Examiner*—Bernard Helfin
*Attorney, Agent, or Firm*—Gordon L. Hart

[57] ABSTRACT

Fluorescers for use in chemiluminescent mixtures having aqueous or organic solvent systems. The compounds have the formula

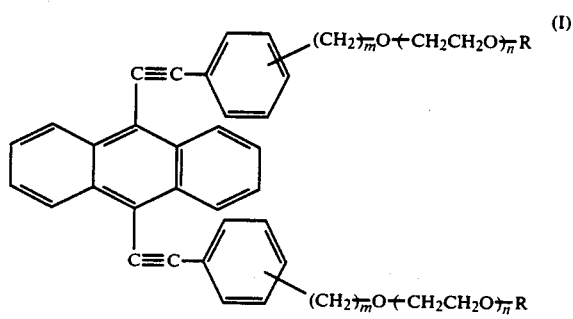

wherein m is an integer from 1 to 5, n is an integer from 1 to 20, and R represents hydrogen, or $C_1$–$C_5$ alkyl. In the preferred embodiments m is 1, n is 5, and R is methyl, or hydrogen.

5 Claims, No Drawings

POLY(ETHYLENEOXY)-SUBSTITUTED-9,10-BIS(-PHENYLETHYNYL)ANTHRACENE MIXTURES

The invention described herein was made in the performance of work supported by the Office of Naval Research (Contract No. N-00014-77-C-0634) and is subject to the provisions of ASPR 7-104.18, December 1969, and ASPR 7-302.23(b) long form, August 1977.

This is a division of application Ser. No. 436,210, filed Oct. 25, 1982.

The invention relates to novel fluorescer compounds, to compositions containing said fluorescers, and processes for producing chemiluminescence, that is, the generation of electromagnetic radiation at wavelengths between 330 and 1000 nanometers by means of a chemical reaction. More particularly, it relates to compositions and processes for producing chemiluminescence in aqueous solutions and emulsions.

The generation of chemiluminescence by the reaction of an ester, or amide, of an oxalic acid with a source of hydrogen peroxide in the presence of a fluorescer compound in aqueous systems has been disclosed in U.S. Pat. Nos. 4,053,430 and 4,282,357. However, the emission intensities and efficiencies of these systems are low. There is a need, therefore, for chemiluminescent compositions having higher emission intensities, light capacities, and efficiencies in aqueous systems.

SUMMARY OF THE INVENTION

The invention provides novel fluorescer compounds represented by formula (I)

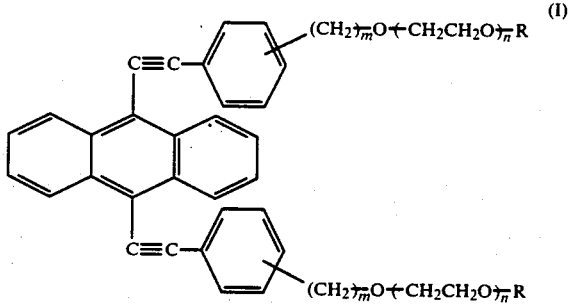

wherein m is an integer from 1 to 5, n is an integer from 1 to 20, and R represents hydrogen, or $C_1$–$C_5$ alkyl. In the preferred embodiments m is 1, n is 5, and R is methyl, or hydrogen.

The novel fluorescers are useful for making chemiluminescent solutions in aqueous or organic solvent liquid medium or in aqueous emulsion.

The invention provides a composition for generating chemiluminescence comprising an aqueous solution of (a) a chemiluminescent reactant soluble in water, (b) a fluorescer of formula (I), and (c) a surfactant in proportions capable of producing enhanced chemiluminescence on reaction with hydrogen peroxide.

The invention also provides a composition for generating chemiluminescence comprising an oil-in-water emulsion of (a) a water-soluble reactant, (b) a fluorescer of formula (I), and (c) a surfactant in proportions capable of producing enhanced chemiluminescence on reaction with hydrogen peroxide.

The invention further comprises chemiluminescent liquid mixtures of ingredients in organic solvent medium.

The invention further provides a composition for generating chemiluminescence comprising a dry mixture of (a) a chemiluminescent reactant soluble in a selected solvent (b) a solid hydrogen peroxide source selected from the group consisting of sodium perborate, potassium perborate, sodium carbonate peroxyhydrate, and histidine perhydrate, (c) a fluorescer of formula (I), and when water is the selected solvent, (d) a surfactant in proportions capable of producing enhanced chemiluminescence when added to water.

For making chemiluminescent compositions in aqueous medium the reactant is preferably a water-soluble ester, or amide, of oxalic acid.

The invention also provides processes for generating chemiluminescence by adding effective amounts of the aforedescribed compositions to a liquid solution of hydrogen peroxide, or a source of hydrogen peroxide.

Aqueous chemiluminescent solutions containing a surfactant produce quantum yields about four times those obtained for processes without the surfactant.

The aqueous chemiluminescent systems of the present invention provide enhanced emission of light which is useful in a wide variety of applications, particularly for providing emergency light at home, on highways, and at sea.

DESCRIPTION

A chemiluminescent reaction mixture contains a water-soluble reactant which generates light by reacting with hydrogen peroxide, or a source of hydrogen peroxide, in the presence of a fluorescer compound of formula (I), and preferably a surface-active agent. The chemiluminescent reactant may be a water-soluble ester or amide of oxalic acid.

Suitable water-soluble esters of oxalic acid which may be used in the present invention were disclosed by Mohan in U.S. Pat. No. 4,053,430.

Illustrative examples of suitable water-soluble esters of oxalic acid include the dihydrochlorides, dihydrobromides, dihydrofluorides, di(trifluoromethane)-sulfonates, dimethanesulfonates, di-p-toluenesulfonates, dimethosulfates and diquaternary ammonium salts of the following compounds:

bis{2,6-dichloro-4-[(2-dimethylaminoethyl)methylsulfamoyl]-phenyl}oxalate,
bis{2,4-dichloro-6-[(2-dimethylaminoethyl)methylsulfamoyl]-phenyl}oxalate,
bis{2-chloro-4-[(2-dimethylaminoethyl)methylsulfamoyl]-phenyl}oxalate,
bis{2 bromo-4-[(2-dimethylaminoethyl)methylsulfamoyl]phenyl}-oxalate,
bis{2,6-dibromo-4-[(2-dimethylaminoethyl)methylsulfamoyl]-phenyl}oxalate,
bis{3-fluoro-4-[(2-dimethylaminoethyl)methylsulfamoyl]-phenyl}oxalate,
bis{2,4-dibromo-6-[(2-dimethylaminoethyl)methylsulfamoyl]-phenyl}oxalate,
bis{2-fluoro-4-[(2-dimethylaminoethyl)methylsulfamoyl]-phenyl}oxalate,
and the like.

The preferred water-soluble ester of oxalic acid is the hydrochloride of {bis 2,4-dichloro-6[(2-dimethylaminoethyl)methylsulfamoyl]phenyl}oxalate.

Suitable water-soluble amides of oxalic acid which may be used in the processes and compositions of this invention are disclosed by Tseng and Rauhut in U.S. Pat. No. 4,282,357.

Illustrative examples of suitable water-soluble amides of oxalic acid include the dihydrochlorides, dihydrobromides, dihydrofluorides, di(trifluoromethane) sulfonates, dimethanesulfonates, dimethosulfates, and ditetrafluoroborates of the following compounds:
N,N'-bis(2-morpholinoethyl)-N,N'-bis(trifluoromethylsulfonyl)oxamide,
N,N'-bis(3-morpholinopropyl)-N,N'-bis(trifluoromethylsulfonyl)oxamide,
N,N'-bis[2-(2-pyridyl)ethyl]-N,N'-bis(trifluoromethylsulfonyl)oxamide,
N,N'-bis[3-(2-pyridyl)propyl]-N,N'-bis(trifluoromethylsulfonyl)oxamide,
N,N'-bis(6-morpholinohexyl)-N,N'-bis(trifluoromethylsulfonyl)-oxamide,
N,N'-bis[2-(4-pyridyl)ethyl]-N,N'-bis(trifluoromethylsulfonyl)oxamide,
N,N'-bis[5-(3-pyridyl)pentyl]-N,N'-bis(trifluoromethylsulfonyl)oxamide,
and the like.

A preferred water-soluble oxamide is 4,4'-{oxalylbis[[(trifluoromethyl)sulfonyl]imono]ethylene}bis(4-methylmorpholinium trifluoromethanesulfonate).

The compounds of formula (I) can be prepared by reacting about two molecular proportions of the lithium salt of an appropriately substituted phenylacetylene with one molecular proportion of anthraquinone to obtain the corresponding 9,10-dihydro-9,10-dihydroxy-9,10-bis(phenylethynyl)anthracene, which is then converted to the 9,10-bis(phenylethynyl)anthracene by methods described by Maulding in U.S. Pat. No. 3,911,038.

Illustrative examples of compounds of formula (I) include the following:
9,10-bis[2-[4-(2,5,8,11,14,17-hexaoxaoctadec-1-yl)phenyl]-ethynyl]anthracene,
9,10-bis[2-[3-(2,5,8,11,14,17-hexaoxaoctadec-1-yl)phenyl]-ethynyl]anthracene,
9,10-bis[2-[4-(3,6,9,12-tetraoxatridec-1-yl)phenyl]ethynyl]-anthracene,
9,10-bis[2-[4-(2,5,8,11-tetraoxapentadec-1-yl)phenyl]ethynyl]-anthracene,
9,10-bis[2-[4-(2,5-dioxahex-1-yl)-phenyl]ethynyl]anthracene,
9,10-bis[2-[4-(2,5-dioxamon-1-yl)-phenyl]ethynyl]anthracene,
9,10-bis[2-[4-(6,9,12,15-tetraoxahexadec-1-yl)phenyl]ethynyl]anthracene,
9,10-bis[2-[4-(12-hydroxy-3,6,9-trioxadodec-1-yl)phenyl]ethynyl]anthracene,
and the like.

The aqueous chemiluminescent reaction mixtures preferably contain about 0.1-5% by weight of an anionic, cationic, or nonionic surface-active agent, herein also referred to as "surfactant," which is not rapidly oxidized by hydrogen peroxide. The terms "surface-active agent," or "surfactant," as used herein, are defined as substances that lower the surface tension of a liquid, or the interfacial tension between two liquids.

Illustrative examples of suitable surfactants include the following:
nonylphenoxy tetraethoxyethanol,
nonylphenoxy hexaethoxyethanol,
nonylphenoxy heptaethoxyethanol,
nonylphenoxy nonaethoxyethanol,
nonylphenoxy decaethoxyethanol,
octylphenoxy nonaethoxyethanol,
isooctylphenoxy decaethoxyethanol,
trimethylnonyl polyethyleneglycol ether,
sodium dodecylsulfate,
sodium diamylsulfosuccinate,
sodium dihexylsulfosuccinate,
sodium bis(2-ethylhexyl)sulfosuccinnate,
sodium bis(tridecyl)sulfosuccinate,
disodium N-octadecylsulfosuccinamate,
sodium 2-ethylhexylsulfate,
sodium heptadecylsulfate,
n-dodecyltrimethylammonium chloride,
and the like.

Preferably, the reaction mixture contains about 0.75-3.5% by weight of a nonionic surfactant, such as a nonylphenoxy polyethoxyethanol containing about 4 to 15 oxyethylene groups per molecule.

The initial molar concentrations (moles per liter of solution) of the oxalic acid ester, or amide, may vary considerably. It is only necessary that it be present in sufficient concentration to obtain chemiluminescence. The initial molar concentration is in the range of $10^{-3}$ to 5, preferably about $10^{-2}$ to 1.0.

The molar concentration of the fluorescer compound used is about $10^{-5}$ to 1, preferably about $10^{-3}$ to $10^{-}$.

The initial molar concentration of the hydrogen peroxide compound used is from about $10^{-3}$ to 10.0, preferably about $10^{-1}$ to 4.0. The mole ratio of hydrogen peroxide to oxalic acid ester, or amide, used ranges from about 0.5 to 100, preferably about 20 to 60.

The reactive ingredients of the chemiluminescent compositions of this invention are kept separated until chemiluminescence is desired, when they may be admixed in a single step or in a series of steps. The order of admixing of the ingredients is usually not critical. The hydrogen peroxide compound, the surfactant, and a fluorescer compound of Formula I may be dissolved in water; the oxalic acid ester, or amide, may be then added as a solid, or in a suitable inert diluent, to initiate chemiluminescence. Alternatively, the oxalic acid ester, or amide, surfactant, and fluorescer compound may be dissolved in water, and the hydrogen peroxide compound added to initiate chemiluminescence. Optionally, a solution of the hydrogen peroxide compound in water may be added to a solid mixture of oxalic acid ester, or amide, surfactant, and fluorescer compound to initiate chemiluminescence.

An illustrative example of a suitable dry solids mixture of ingredients contains the following: 13.23% by weight of 4,4'-[oxalylbis[(trifluoromethylsulfonyl)-imino]ethylene]bis[4-methyl-morpholinium trifluoromethanesulfonate], (METQ), 2.12% by weight of the product of Example 2, 2.65% by weight of Tergitol ® Nonionic Surfactant NP-13, and 82.00% by weight of sodium perborate. Water is added to the dry mixture to dissolve the ingredients and initiate chemiluminescence.

If the fluorescer compound is water-insoluble, it may be dissolved in a suitable inert water-immiscible organic solvent, such as cyclohexane, and the solution added to an aqueous mixture of a hydrogen peroxide source, an effective amount of a surfactant, and a water-soluble reactant to produce a chemiluminescent emulsion.

The hydrogen peroxide source employed in the compositions and processes of this invention may be an aqueous solution of hydrogen peroxide per se, or a hydrogen peroxide-producing compound, such as sodium perborate, potassium perborate, sodium carbonate peroxyhydrate, histidine perhydrate, and the like.

Variation of the pH of the reaction medium from about 3.0 to about 8.4 shows that the quantum yield is dependent on the pH. The maximum quantum yield is obtained at a pH of 3.

Superior intensity of chemiluminescence is obtained when the final mixture producing the luminescence is maintained at a temperature from about −10° to 50° C., preferably from about 15° to 40° C.

The invention is described in more detail by the following examples in which concentrations in moles per liter are indicated by the letter "M." All parts, and percentages, are by weight unless otherwise indicated. In all of the examples which follow, the aqueous solution of hydrogen peroxide employed contains 1.75 moles per liter of hydrogen peroxide, and 0.0012 mole per liter of sodium salicylate, which catalyzes the reaction.

EXAMPLE 1

Preparation of a Mixture of 3 (and 4)-(2,5,8,11,14,17-Hexaoxaoctadecyl)phenylacetylene To a solution of 3 (and 4)-(chloromethyl)phenylacetylene (15.0 grams; 0.10 mole) and 3,6,9,12,15-pentaoxahexadecanol (27 mls; 0.1 mole) is added 50% aqueous sodium hydroxide (54 mls; 1.02 mole), while externally cooling it to control the resulting exotherm. The addition of tetrahydrofuran (80 mls) to the reaction mixture gives a stirrable suspension to which benzyltriethylammonium chloride (1.14 gram; 0.005 mole) is added. The resulting suspension is stirred at 40° C. for 18 hours, and then filtered. The dark upper layer of the filtrate is extracted with tetrahydrofuran (3×200 mls) and the ethereal extract is evaporated to obtain a dark oil which is subsequently dissolved in dichloromethane (500 mls). The solution is extracted with 5% aqueous acetic acid (100 mls), and then with water (2×100 mls). The organic layer is then dried over anhydrous magnesium sulfate, treated with Darco® Decolorizing Carbon (ICI Americas, Inc.) and evaporated after removing the activated carbon to obtain a light yellow oil containing some water. The oil is heated in boiling 2,2-dimethoxypropane for 90 minutes to remove the water, and the solvent is evaporated to obtain the desired product as a dry oil (34.2 grams; 93% of theoretical).

Calculated for $C_{20}H_{30}O_6$: C,65.57%; H,8.20%. Found: C,63.63%; H,83.03%.

The nuclear magnetic resonance spectrum of the product of Example 1 in $CDCl_3$ shows the presence of 4 aromatic protons at 7.5–7.1 ppm, 2 benzylic protons at 4.5 ppm, 20 protons for the ethylene groups at 3.8–3.5 ppm, 3 protons for the methoxyl group at 3.3 ppm, and a single acetylenic proton at 3.2 ppm.

The infrared absorption spectrum in neat oil shows strong absorptions of 3240, 2860, 1440, and 1100 cm$^{-1}$.

The above-described spectral data are consistent with the expected structure.

EXAMPLE 2

Preparation of a Mixture of 9,10-Bis[2-[3(and 4)-(2,5,8,11,14,17-hexaoctadec-1-yl)phenyl]ethynyl]anthracene A mixture of the product of Example 1 (18.3 grams; 0.05 mole) and lithium amide (1.3 grams; 0.055 mole) in dioxane (75 mls) is refluxed, under a nitrogen atmosphere, for 3 hours. The resulting solution is cooled to 20° C., and anthraquinone (5.2 grams; 0.025 mole) is added thereto, along with 25 mls of dioxane; refluxing is then continued for 4 hours. The reaction mixture is cooled to room temperature and aqueous acetic acid (15 mls), followed by stannous chloride dihydrate (11.3 grams; 0.05 mole) in dimethylformamide (35 mls), are added thereto. The resulting solution is stirred at room temperature for 20 hours, and then cooled in an ice bath. A gummy material forms upon the addition of glacial acetic acid (50 mls), 5N sulfuric acid (50 mls), and water (200 mls). The aqueous layer is heated and extracted with hot toluene (5×70 mls), as the upper layer of a rapidly stirred two-phase system. The combined toluene extracts are treated hot with Magnesol* (trademark FMC Corporation), then Darco® Decolorizing Carbon, and finally magnesium sulfate. Evaporation of the clarified solution leaves a dark oil which is purified by high-performance liquid chromatography (3:1, ethyl acetate:acetone) to obtain an orange oil which shows a single spot by thin layer chromatography.

Calculated for $C_{54}H_{66}O_{12}$: C,71.50%; H,7.33%. Found: C,68.73%; H,6.90%.

The nuclear magnetic resonance spectrum of the product of Example 2 in $CDCl_3$ reveals the 16 aromatic protons as two sets of complex multiplets at 8.8–8.4 ppm and 7.8–7.2 ppm, the 4 benzylic protons at 4.7–4.4 ppm, the 40 protons of the ethylene groups at 3.7–3.4 ppm, and the 6 methoxyl protons at 3.2 ppm.

The infrared absorption spectrum in neat oil shows strong absorptions at 2860, 1595, 1435, 1345, 1240, 1100, 770, 735, and 695 cm$^{-1}$.

The above-described spectral data are consistent with the expected structure.

EXAMPLES 3 AND 4

Determination of Chemiluminescence

Aqueous hydrogen peroxide (2.5 mls; 1.75M), containing 0.094 gram of Deceresol® Surfactant NI conc. and sodium salicylate (1.2×10$^{-3}$M) is added to a cuvette containing 4,4′-[oxalylbis[(trifluoromethylsulfonyl)imino]ethylene]bis [4-methylmorpholinium trifluoromethanesulfonate] (0.10 gram) and the product of Example 2 in amounts to provide molar concentrations of 4×10$^{-2}$ and 1×10$^{-2}$ of those compounds, respectively. The reaction mixture is mixed thoroughly and the emission intensity is measured at the emission peak (λ max) of the fluorescer versus time by means of a spectroradiometer-luminometer similar to that described by Roberts and Hirt [Appl. Spectrosc., 21, 250 (1967)] modified with a Jarrell-Ash Model 82-410 grating monochromator and an RCA C31034 photomultiplier with a gallium arsenide photocathode operated at 1300V with dry ice cooling. Raw data are recorded digitally on a Hewlett-Packard 5150A thermal printer. Spectral response is corrected by calibration against a standard tungsten lamp. Absolute light intensities are obtained by deriving calibration constants based on the accepted fluorescence quantum yield (0.55) for quanine sulfate, as reported by Melhuish [N.Z. Sci. Tech., B, 37, 142 (1955)], in 0.1N $H_2SO_4$, and by ferrioxalate actinometry [Hatchard et al., Proc. R. Soc. London, Ser. A, 235, 518 (1956) of the exciting light. The light capacity (the light output in lumen hours per liter of emitting solution) is related to the chemiluminescence brightness and lifetime as described in U.S. Pat. No. 3,816,326.

TABLE I

| Example | Fluorescer | λMax (nm) | Light Capacity[a] | Percent[b] Quantum Yield | $T_{75}$[c] |
|---|---|---|---|---|---|
| | | AQUEOUS SYSTEMS | | | |
| 3 | Product of Example 2 (with surfactant) | 565 | 8.8, 9.7 | 0.88, 0.97 | 4.6, 4.5 |
| 4 | Product of Example 2 (without surfactant) | 565 | 1.4 | 0.23 | 3.88 |
| 5 | Product of Example 2 (with surfactant and cyclohexane) | 590; 595 | 5.28; 5.17 | 0.79; 0.97 | 9.8; 10.2 |
| | | ORGANIC SOLVENT SYSTEMS | | | |
| 7 | Product of Example 2 | 510 | 361 | 12.16 | 138 |
| 8 | Product of Example 6 | 515 | 246 | 8.61 | 280 |

[a]Lumen hours per liter
[b]Einsteins per mole × 100
[c]Time (in minutes) required for 75% of the total light to be emitted Chemiluminescence percent quantum yields (einsteins per mole of reactant × 100) are calculated by monitoring the intensity decay at the emission maximum and calculating the intensity at each time interval in einsteins per second from the chemiluminescence spectrum. Chemiluminescence spectra are then corrected for intensity decay. The total area under the decay curve is calculated by using a combination of a Simpson's rule integration and an exponential extrapolation to infinite time as described by Roberts and Hirt. Data are processed by a Digital Equipment Corp. PDP 11/40 computer.

In the manner described above, a comparison determination is also carried out without the surfactant.

The results obtained are shown in Table I under Examples 3 and 4, respectively. The results show that significantly higher light capacity and quantum yield are obtained in the presence of the surfactant.

EXAMPLE 5

An aqueous solution of hydrogen peroxide (2.3 mls; 1.75M) is added to a cuvette containing 0.0251 gram of the product of Example 2, 0.1 gram of METQ, 0.5 ml of cyclohexane, and 0.0221 gram of DECERESOL® Surfactant NI Conc. The materials are mixed thoroughly at ambient temperature to provide an emulsion having an initial concentration of 0.0404M for the METQ, and a concentration of 0.01M for product of Example 2. The chemiluminescent characteristics obtained as in Examples 3 and 4 are shown in Table 1.

Fluorescers having the formula I may also be used as fluorescers in chemiluminescent mixtures made with organic solvents of the more conventional kinds described in numerous prior art patents and other literature. An advantage of some of the fluorescers defined by formula I is their utility in both aqueous and organic solutions of chemiluminescent mixtures. Such use in an organic solvent system is illustrated in Example 7 and a similar fluorescer is compared in Example 6.

COMPARISON EXAMPLE 6

Preparation of a Mixture of 9,10-Bis[3(and 4)-(hydroxymethyl)phenylethynyl]anthracenes To a stirred solution of a mixture of 3 (and 4)-allyloxymethyl)phenylacetylenes (5.2 grams; 0.01 mole) in dry dioxane (75 mls) is added selenium (IV) dioxide (2.4 grams; 0.022 mole) and glacial acetic acid (1.8 mls; 0.03 mole), under nitrogen. After stirring at reflux temperature for 3½ hours, analysis by thin layer chromatography (50/50 methylene chloride: ethyl acetate) reveals almost complete absence of the starting material. The hot solution is filtered to remove a black solid, which is washed with hot dioxane (2×50 mls). Evaporation of the filtrate and washings yields an orange semi-solid.

Elution of this material through a Waters Prep 500 High Performance Liquid Chromatograph (2:1 chloroform/tetrahydrofuran) yields the desired compound as the most polar fraction, m.p. 160°–169° C.

Anal. Calculated for $C_{32}H_{22}O_2$: C,87.67%; H,5.02%. Found: C,85.07%; H,5.55%.

The nuclear magnetic resonance and infrared spectra of the product are consistent with the proposed structure.

EXAMPLES 7 AND 8

Determination of Chemiluminescence

Solutions of 7.5 mls of bis(6-carbopentoxy-2,4,5-trichlorophenyl)oxalate (CPPO) and fluorescers from Examples 2 and 6 are made in dibutyl phthalate. Each solution is mixed with 2.5 mls of a peroxide component which consists of hydrogen peroxide and sodium salicylate in 80% dimethyl phthalate-20% (by volume) tertiary butanol. Each of the chemiluminescent reaction mixtures contains initial concentrations of 0.38 M hydrogen peroxide, $1.56 \times 10^{-4}$M sodium salicylate, 0.10M CPPO, and $2.25 \times 10^{-3}$M of the fluorescer. Quantitative measurements of the chemiluminescence of the solutions are carried out by means of a Hirt-Roberts radiometer-spectrophotometer using the procedure described in the Journal of Organic Chemistry, Volume 44, page 4115 (1979). The results are shown in Table I. The fluorescer compound of Example 2 provided significantly higher light capacity and quantum yield than the comparison fluorescer (Example 6 which was selected for comparison because it is a fluorescer compound differing by the terminal group on the phenyl radical.

We claim:

1. A chemiluminescent reaction mixture comprising a compound defined by the structural formula

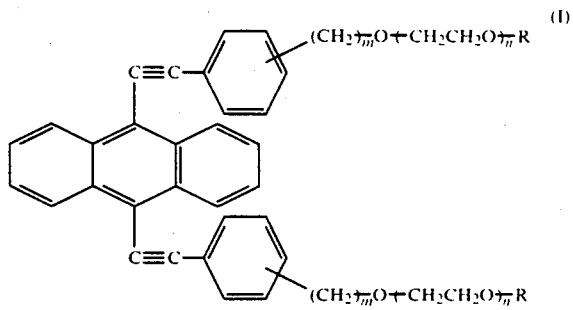

(I)

wherein m is an integer from 1 to 5, n is an integer from 1 to 20 and R represents hydrogen or $C_1$ to $C_5$ alkyl, as a fluorescer component in said mixture.

2. A chemiluminescent reaction mixture defined by claim 1 comprising water as a solvent for said mixture.

3. A chemiluminescent reaction mixture defined by claim 1 comprising a non-aqueous organic liquid as solvent for said mixture.

4. A chemiluminescent reaction mixture defined by claim 2, further comprising a surfactant.

5. A chemiluminsecent reaction mixture defined by claim 4 wherein the surfactant is a nonionic surfactant.

* * * * *